United States Patent [19]

Shulman

[11] 4,209,468

[45] Jun. 24, 1980

[54] TRIARYL-PHOSPHINE COMPOUNDS

[75] Inventor: Joel I. Shulman, Cincinnati, Ohio

[73] Assignee: The Procter & Gamble Company, Cincinnati, Ohio

[21] Appl. No.: 879,655

[22] Filed: Feb. 21, 1978

Related U.S. Application Data

[62] Division of Ser. No. 781,832, Mar. 28, 1977, Pat. No. 4,098,911.

[51] Int. Cl.$^2$ .................. C07D 105/02; C07D 107/02
[52] U.S. Cl. .............................. 568/13; 260/570.5 P; 426/547; 426/601; 568/16; 568/17
[58] Field of Search .................. 260/570.5 P, 606.5 P

[56] References Cited

U.S. PATENT DOCUMENTS

| 3,652,678 | 3/1972 | Allum et al. ...................... 260/606.5 |
| 4,098,911 | 7/1978 | Shulman ........................... 426/601 X |

*Primary Examiner*—Robert V. Hines
*Attorney, Agent, or Firm*—Jerry J. Yetter; Rose Ann Dabek; Richard C. Witte

[57] ABSTRACT

Oligomeric or polymeric triaryl- and substituted triaryl-phosphine compounds which are non-digestible and non-absorbable by animals are disclosed. These compounds act as antioxidants by inhibiting the buildup of hydroperoxides of unsaturated fatty acids, e.g., in foods.

4 Claims, No Drawings

TRIARYL-PHOSPHINE COMPOUNDS

This is a division of application Ser. No. 781,832, filed Mar. 28, 1977 and now U.S. Pat. No. 4,098,911.

BACKGROUND OF THE INVENTION

Fats and oils which contain fatty acids are oxidized in the presence of oxygen to hydroperoxides. These hydroperoxides further decompose to form either polymers, gummy materials, aldehydes, ketones or acids. The presence of hydroperoxides and their decomposition products causes fats and oils and foods containing fats and oils to develop off-flavors and malodors.

Antioxidants, for example, the tocopherols, BHA, BHT, TBHQ and citric acid inhibit the oxidation of unsaturated fatty acids, but do not prevent the formation and decomposition of hydroperoxides. Generally, food antioxidants act either by chelating heavy metals which can catalyze autoxidation, or by interrupting the free radical chain mechanisms of autoxidation.

Trivalent phosphorus compounds have been used as antioxidants in plastics, gasoline, and in other non-food products. However, monomeric phosphines are toxic and not suitable for use in edible fats and oils.

It is an object of this invention to provide trivalent phosphorous compounds which are effective in inhibiting the hydroperoxide formation in fatty materials containing fatty acids, especially fats and oils.

It is another object of this invention to provide food antioxidants which are non-digestible and non-absorbable and thus, non-toxic.

SUMMARY OF THE INVENTION

Oligomeric or polymeric compounds characterized by the moiety

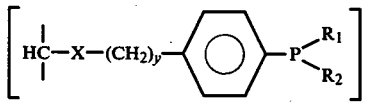

wherein X is selected from the group of oxygen, nitrogen or sulfur, $R_1$ and $R_2$ are each selected from the group of aryl and substituted aryl and y is an integer from 1 to 4 are disclosed. Food compositions comprising unsaturated fats or oils stabilized with an effective amount of the polymeric triaryl- or substituted triarylphosphine compounds are also disclosed.

DETAILED DESCRIPTION OF THE INVENTION

This invention relates to polymeric (including "oligomeric") triaryl- or substituted triarylphosphine compounds which are especially useful for prohibiting the build-up of hydroperoxides in foods, particularly fats and oils. The food compositions herein comprise a safe and effective amount of the polymeric triaryl- or substituted triarylphosphine compounds.

By "effective amount" herein is meant an amount which substantially prevents the build-up of hydroperoxides in materials, especially fats and oils, containing unsaturated fatty acids. For food use in fats and oils, an amount in the range of about 10 to about 1000 ppm is effective and safe for ingestion by humans and lower animals. The amount used will depend upon several factors, including the amount of unsaturation in the fatty acid fats or oils, and the presence of other antioxidant materials in the fat or oil.

By "comprising" herein is meant that various other compatible ingredients may be present in the compositions in such a proportion as will not adversely affect the stability and the hydroperoxide inhibiting effectiveness of the basic food composition. The term "comprising" thus encompasses and includes the more restrictive terms "consisting of" and "consisting essentially of" within its scope.

By "aryl" herein is meant hydrocarbon substituents containing the aromatic nucleus, e.g., phenyl or naphthyl.

By "substituted aryl" herein is meant an aryl moiety in which a hydrogen has been replaced by an alkyl radical, an alkoxy radical, a thioalkyl radical, a halogen or other substituent which, itself, will not react with oxygen to produce undesirable hydroperoxide compounds. When the compounds herein are used as antioxidants in foods containing fats or oils, the phenyl group is preferred.

The compounds useful in this invention are oligomeric or polymeric compounds containing the moiety

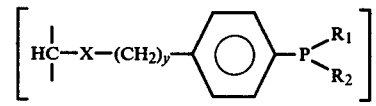

wherein X is selected from the group of oxygen, sulfur, and nitrogen, and $R_1$ and $R_2$ are each selected from the group of aryl and substituted aryl and y is an integer from 1 to 4.

Preferred oligomeric and polymeric triarylphosphines and substituted triarylphosphine compounds for use as antioxidants are those derived from polyols. These polyol-based triarylphosphine polymers are preferred because they can be made from readily available starting material.

Compounds of the formula

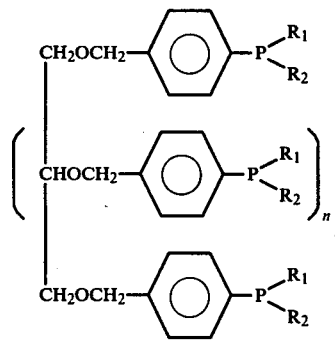

where n is an integer from 0 to 4 and $R_1$ and $R_2$ are each selected from the group of aryl or substituted aryl, are easily prepared from various polyols including: glycols, glycerol, sugar alcohols.

Glycols which are useful for the practice of this invention are ethylene glycol, 1,2-propylene glycol, 1,3-propylene glycol, the butyl glycols, the pentyl glycols, and others. Ethylene glycol and glycerol are most preferred for use herein.

The following reaction scheme is used:

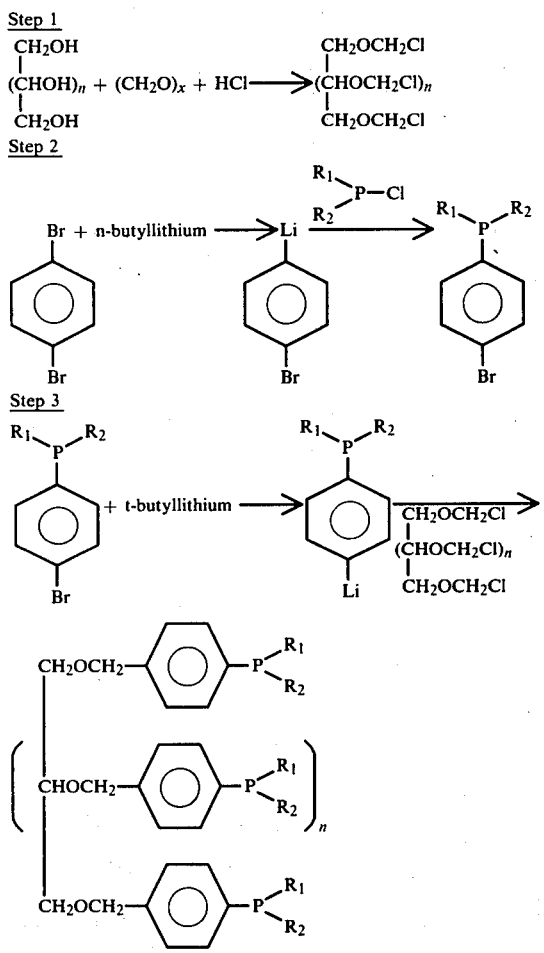

Step 1

$$\begin{array}{l} CH_2OH \\ | \\ (CHOH)_n + (CH_2O)_x + HCl \longrightarrow \\ | \\ CH_2OH \end{array} \quad \begin{array}{l} CH_2OCH_2Cl \\ | \\ (CHOCH_2Cl)_n \\ | \\ CH_2OCH_2Cl \end{array}$$

Step 2

Step 3

Suitable diarylphosphine halides are those in which $R_1$ and $R_2$ are each selected from the group of phenyl, methylphenyl, ethylphenyl, methoxyphenyl, ethoxyphenyl, propoxyphenyl, chlorophenyl, bromophenyl, naphthyl, and the like. Preferred for use herein are those substituted aryls in which the alkyl substituent is $C_1$ to $C_4$, alkoxy substituent containing from $C_1$ to $C_4$, and the halogen derivatives. The most preferred phosphines for use in this reaction is that phosphine where $R_1$ and $R_2$ are both phenyl.

The same reaction sequence can be used to prepare related phosphine compounds which are derivatives of sugars, including monosaccharides, disaccharides, trisaccharides, and tetrasaccharides, among others, or other polyols, for example, pentaerythritol, and of dithiols or polythiols.

The moiety

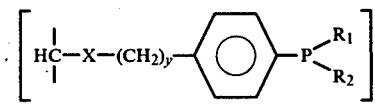

wherein X is sulfur or nitrogen, and y is an integer from 1 to 2, and $R_1$ and $R_2$ are each selected from the group of aryl and substituted aryl can be prepared by a reaction sequence similar to that used to prepare the oxygen compounds. The phosphine compound formed at Step 2 can be reacted with the moiety

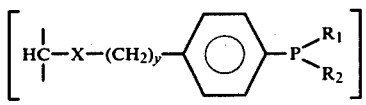

wherein X is selected from the group of sulfur or nitrogen.

The previously disclosed polymeric phosphine compounds are useful for suppressing the formation of hydroperoxides of fatty acids. As such, these compounds, and other compounds which are polymeric triaryl- or substituted triarylphosphines can be used in foods or fats and oils which contain fatty acids or esters thereof to stabilize them against oxidation by atmospheric oxygen. The compounds which are particularly useful for this function are those containing the moiety

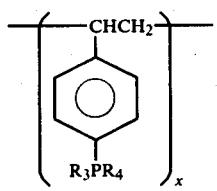

wherein X is selected from the group of oxygen, nitrogen or sulfur, y is an integer from 1 to 4 and $R_1$ and $R_2$ are each selected from the group of aryl or substituted aryl; and those of the general formula $$\underset{x}{\underbrace{\left(-CHCH_2-\right)}}\begin{array}{c}\\ \text{phenyl}\\ |\\ R_3PR_4 \end{array}$$

wherein x is an integer of from 2 to about 15, preferably 3 to 10, and $R_3$ and $R_4$ are each selected from the group of aryl and substituted aryl.

The hydrocarbyl polymeric phosphine compounds can be prepared by the free radical or ionic polymerization of the corresponding styryl or alkylene derivative.

Food antioxidant compounds are particularly useful in oils and fats which contain unsaturated fatty acids. Oils which are polyunsaturated, especially safflower oil, sunflower seed oil, soybean oil and corn oil are particularly susceptible to hydroperoxide formation. Foods containing these oils, mixtures thereof, or the corresponding hydrogenated oils, need to be protected by an antioxidant.

The polymeric aryl- or substituted arylphosphine compounds are preferably those with a molecular weight from about 600 to about 3000. These compounds are not digested and are not absorbed by the animal ingesting them.

Those compounds with molecular weights substantially above these numbers are not soluble in the oil or the foods and thus are not effective in preventing hydroperoxide formation. Those polymeric phosphine compounds below about 600 in molecular weight are easily metabolized by animals and thus could produce toxic compounds in the animals' digestive system.

The following examples are illustrative of the invention, but are not meant to be limiting thereof.

EXAMPLE I

Preparation of 1,2,3-tris(p-diphenylphosphinobenzoxy)propane

Step A. A mixture of 114 g of glycerol and 148.5 g of paraformaldehyde in a three-necked flask is stirred mechanically until a thick paste is formed. With stirring and cooling by an external ice bath, excess hydrogen chloride gas is bubbled through the slurry until the mixture becomes very fluid and no more hydrogen chloride is absorbed. The two phases are separated and the lower, cloudy layer is dried overnight over anhydrous $CaCl_2$. Filtration through glass wool and distillation affords 130.5 g of 1,2,3-tris(chloromethoxy)propane, bp 168°–170° C. (18 mm).

Step B. To 1.0 mole of n-butyllithium in hexane at −78° C. under an inert atmosphere is added dropwise and with efficient stirring 236 g of p-dibromobenzene in dry tetrahydrofuran (total volume 500 ml). The resulting solution is stirred at −78° C. for 1 hour, then treated dropwise at this temperature with 220.5 g of chlorodiphenylphosphine. When this addition is complete, the mixture is allowed to warm to room temperature, then solvent is removed under vacuum. The residue is triturated with two 400-ml portions of methanol, then distilled through a Vigreux column. The cut with bp 165°–170° C. (0.15 mm) is recrystallized from ethanol to give 100.5 g of p-diphenylphosphinobromobenzene, mp 78°–80° C.

Step C. A mixture of 110 ml of ca. 1M t-butyllithium in hexane and 180 ml of dry tetrahydrofuran is cooled to −70° C. under an inert atmosphere. To this is added dropwise a solution of 28 g of the product of Step B in 200 ml of tetrahydrofuran, keeping the reaction temperature below −60° C. Additional small aliquots (1 g) of the product of Step B are added until thin-layer chromatographic analysis shows this compound to be present in excess (in the present instance, another 3 g). Then a 6.5 g portion of the product of Step A in 5 ml of tetrahydrofuran is added and the solution is warmed to ambient temperature and stirred for 16 hours. The reaction mixture is poured into 1 l of water, the organic layer is separated, and the aqueous layer is extracted with three 100-ml portions of peroxide-free ethyl ether. The combined organic layers are washed with water, then brine, dried over anhydrous $MgSO_4$, and concentrated under vacuum to leave 28.7 g of crude product as a syrup. Preparative layer or column chromatography on silica gel affords high purity 1,2,3-tris(p-diphenylphosphino)benzoxypropane.

Analysis: Calcd. for $C_{60}H_{53}O_3P_3$: C, 78.76%; H, 5.84%; P, 10.16%. Found: C, 78.64%; H, 5.99%; P, 10.20%.

The proton NMR Spectrum ($CDCl_3$) showed bands at approximately 3.5 to 3.9 (m, 5H), 4.50 (s, 4H), 4.65 (s, 2H), and 7.25 (m, 42H).

Mass spectrometry confirmed the molecular weight of the compound as 914.

When the product of Step C of Example I is added at 500 ppm to deodorized safflower oil and the oil is heated at 60° C. with air bubbling through it, the initiation time for peroxide build-up is increased. No titratable peroxide can be observed in the oil for at least 51 hours. During this time deodorized safflower oil alone reaches a peroxide value of 5.9 meq/kg.

When the product of Step C of Example I is added at 199 ppm to deodorized soybean and the oil is heated at 60° C. in a loosely capped can for eight days, the peroxide value of the oil reaches 3.8 meq/kg. During this time deodorized soybean oil without addition of the product of step C reaches a peroxide value of 16.2 meq/kg.

When an antioxidant product made according to this example, but containing a radioactive carbon-14 tracer, is fed to rats, all the radioactivity is excreted in the rats' feces. Less than 0.1% of the fed radioactivity appears in the lymphatic fluid and in expired carbon dioxide, thus indicating that the antioxidant is not absorbed from the gastrointestinal tract.

EXAMPLE II

Preparation of poly(p-diphenylphosphino)styrene

To 2.42 g (8.4 mmol) of p-diphenylphosphinostyrene (as prepared by R. Rabinowitz and R. Marcus, *J. Org. Chem.*, 26, 4157 (1961)), in a two-necked round bottom flask is added 6.0 ml of dry benzene. This solution is degassed on a high vacuum line, and, while frozen, the mixture is then placed under nitrogen. The mixture is allowed to partially melt. Then with stirring 0.88 ml (1.4 mmol) of 1.6 M n-butyllithium in hexane is added rapidly via syringe. Within 45 seconds, 0.30 ml of distilled degassed tetrahydrofuran is added to the yellow solution; this serves to activate the anionic initiator. The solution rapidly turns dark. Stirring is continued for 30 minutes, then the reaction is quenched by adding 0.12 ml of methanol. The solution is washed with three 12-ml portions of water and the resulting benzene solution is freeze-dried to leave 2.47 g (100%) of colorless powder.

Analysis: Calcd. for $C_{20}H_{17}P$: P, 10.7% Found: P, 10.7%, 10.7%. Molecular weight (by vapor phase osmometry in benzene): 2400. Melting point, 99°–101° C.

The NMR spectrum ($CDCl_3$) showed an aromatic-:aliphatic proton ratio of 3.3:1. This corresponds to one butyl group per eight styryl groups, or a degree of polymerization of 8. The molecular weight data demand a degree of polymerization of 8.

When the product of Example II is added at 500 ppm to deodorized safflower oil and the oil is heated at 60° C. with air bubbling through it, the initiation time for peroxide build-up is increased. No titratable peroxide can be observed in the oil for at least 46 hours. After 70 hours, the peroxide value of the oil reaches 1.2 meq/kg. Under these conditions, deodorized safflower oil without the addition of the product of Example II reaches a peroxide value of 29.8 meq/kg after 70 hours.

I claim:

1. A polymeric triaryl-phosphine or a polymeric substituted triaryl phosphine of the formula:

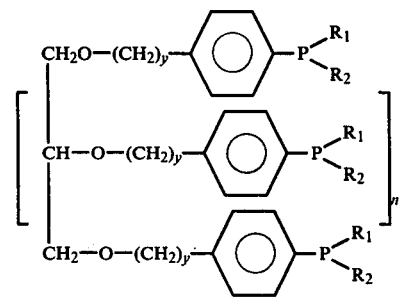

wherein $R_1$ and $R_2$ are each selected from the group of aryl and substituted aryl, n is an integer from 0 to 4, and y is an integer from 1 to 4; or

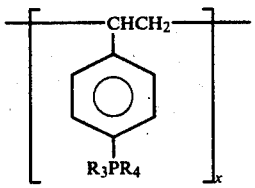

wherein x is an integer of from 2 to about 15 and $R_3$ and $R_4$ are each selected from the group of aryl and substituted aryl.

2. A compound according to claim 1 wherein $R_1$ and $R_2$ are selected from the group of phenyl, methylphenyl, ethylphenyl, methoxyphenyl, ethoxyphenyl, chlorophenyl and bromophenyl.

3. A polymeric phosphine compound according to claim 1 having the formula:

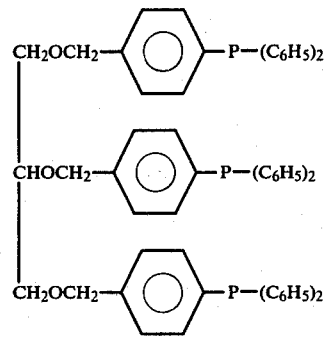

4. A polymeric phosphine compound according to claim 1 having the formula

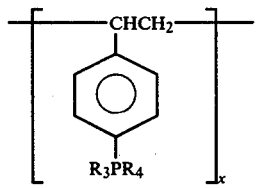

wherein $R_3$ and $R_4$ are each phenyl and x is an integer from 3 to 10.

* * * * *